United States Patent [19]

Giebel et al.

[11] 4,428,674
[45] Jan. 31, 1984

[54] METHOD AND INSPECTION APPARATUS FOR INSPECTING AN OBJECT, IN PARTICULAR A BOTTLE

[76] Inventors: Hayo Giebel, Lindemoosweg 25, Traubing, Fed. Rep. of Germany, D-8131; Heinz Gutschale, Brunnerstrasse 9, München, Fed. Rep. of Germany, D-8000

[21] Appl. No.: 286,350

[22] Filed: Jul. 23, 1981

[30] Foreign Application Priority Data

Jul. 30, 1980 [DE] Fed. Rep. of Germany ....... 3028942

[51] Int. Cl.³ ............................................ G01N 21/90
[52] U.S. Cl. .................................. 356/240; 250/223 B
[58] Field of Search ............... 356/239, 240; 250/562, 250/563, 572, 223 B; 209/526, 577; 358/106

[56] References Cited

U.S. PATENT DOCUMENTS

| | | | |
|---|---|---|---|
| 3,739,184 | 6/1973 | Katsumata et al. | 250/223 B |
| 3,743,431 | 7/1973 | Cushing et al. | 250/572 X |
| 3,746,784 | 7/1973 | Van Oosterhout | 250/223 B X |
| 3,886,356 | 5/1975 | Gomm et al. | 356/240 X |
| 3,887,284 | 6/1975 | Gender et al. | 356/240 |
| 3,920,970 | 11/1975 | Slaker | 250/563 X |
| 4,140,901 | 2/1979 | Fischer et al. | 250/223 B |
| 4,172,524 | 10/1979 | Holm et al. | 250/223 B X |
| 4,223,346 | 9/1980 | Neiheisel et al. | 250/572 X |

Primary Examiner—William L. Sikes
Assistant Examiner—Matthew W. Koren
Attorney, Agent, or Firm—Christie, Parker & Hale

[57] ABSTRACT

A method of and apparatus for inspecting an object, in particular a bottle, which is irradiated by a radiation that is received and converted into an electrical video-signal which is converted into a digital signal, points of fault in the object being established by alterations in intensity between the digital signals from two adjacent image spots, characterized in that:

(1) only alterations in intensity which exceed a definite threshold level are recorded as the start of a point of fault and the end of a point of fault;
(2) for each of these points of fault certain characteristic quantities such, e.g., as mean relative blackening, maximum relative blackening, width of the point of fault and/or overall extent of the point of fault, are determined;
(3) the characteristic quantities are divided up into different classes corresponding with their magnitudes;
(4) the frequency distribution of the occurrence of the characteristic quantities in the different classes is established by adding; and
(5) the frequency distribution established is correlated with predetermined frequency distributions in order to decide about the quality of the object.

13 Claims, 8 Drawing Figures

METHOD AND INSPECTION APPARATUS FOR INSPECTING AN OBJECT, IN PARTICULAR A BOTTLE

The invention refers to a method (hereinafter referred to as of the kind described) of inspecting an object, in particular a bottle, which is irradiated by a radiation that is received and converted into an electrical videosignal which is converted into a digital signal, points of fault in the object being recognised by alterations in intensity between the digital signals from two adjacent image spots, as well as an inspection apparatus for carrying out the method.

In the case of one such method and inspection apparatus known from the West German O/S No. 29 38 235 bottles, for example, are tested by means of light radiation for foreign bodies and damage and also for their contours. The videosignals generated by a photoelectric image-converter are converted by means of an analogue-digital converter into digital signals which are stored temporarily in a register. An output signal from the register is compared with an instantaneous output signal from the analogue digital converter in order to establish an alteration in intensity between two adjacent image spots of the videosignal. Through the processing of the videosignal in such a way that alterations in intensity between adjacent image spots are established from time to time, the influence of different average brightnesses caused, e.g., because of different colouring of the bottles, are excluded. If such a method is made use of for the automatic testing of bottles for foreign bodies and damage in a beverage filling installation, it has been found that, especially in the case of high transit speeds of the bottles which are to be tested, it does not work with the necessary accuracy, so that either bottles having unacceptable points of fault are let through or else a large number of those bottles, which would still satisfy the quality requirements imposed, are excluded as faulty.

The object of the invention is to develop further a method of the kind described in such a way that the quality requirements predetermined at any time are maintained with great reliability. Furthermore it is desirable for a so-called intelligent inspection apparatus to be created for the performance of the method.

In accordance with the invention, a method of the kind described is characterized in that:

(1) only alterations in intensity which exceed a definite threshold level are recorded as the start of a point of fault and the end of a point of fault;

(2) for each of these points of fault certain characteristic quantities are determined;

(3) the characteristic quantities are divided up into different classes corresponding with their magnitudes;

(4) the frequency distribution of the occurrence of the characteristic quantities in the different classes is established by adding; and (5) the frequency distribution established is correlated with predetermined frequency distributions in order to decide about the quality of the object.

The invention also includes an inspection apparatus for carrying out the new method and having a photoelectric image-converter, an analogue-digital converter for the output signal from the image-converter, a register for temporary storage of the digital signal and a comparator for comparing the output signal from the analogue-digital converter with an output signal from the register, characterized by:

(a) an adaptive threshold regulator for step (1) of the method;

(b) an initial-intensity store, an intensity integrator, a maximum-detector as well as a width-meter for step (2) of the method;

(c) quantizers connected after the foregoing respectively, for step (3) of the method;

(d) a histogram store for step (4) of the method; and (e) a frequency correlator for step (5) of the method.

In the practice of the invention, by means of an adaptive threshold regulator, only those alterations in intensity in the digitalized videosignal previously coded by 8 bits, which exceed a definite threshold level, get registered as the start of a point of fault and the end of a point of fault. This threshold level is moreover set according to the average brightness of the image of the object. From each of these points of fault definite characteristic quantities such as the means relative blackening, the maximum relative blackening, the widths of the point of fault and/or the overall extent of the point of fault are determined. The characteristic quantities so determined are divided up to correspond with their magnitude or respectively their value into preferably three different classes. By adding these different characteristic quantities occurring in the three different classes a frequency distribution is established across the whole image of the object. The frequency distribution so established is correlated with a predetermined frequency distribution in order to arrive at a decision about the quality of the object being tested.

Although the method in accordance with the invention and also the inspection apparatus for the performance of the method may be employed with different forms of electromagnetic or acoustic radiation for inspecting very different objects, they serve preferably for the testing of bottles, for foreign bodies or damage, by means of light radiation.

An example of apparatus in accordance with the invention is explained with the aid of the accompanying drawings, in which.

Figure 1:
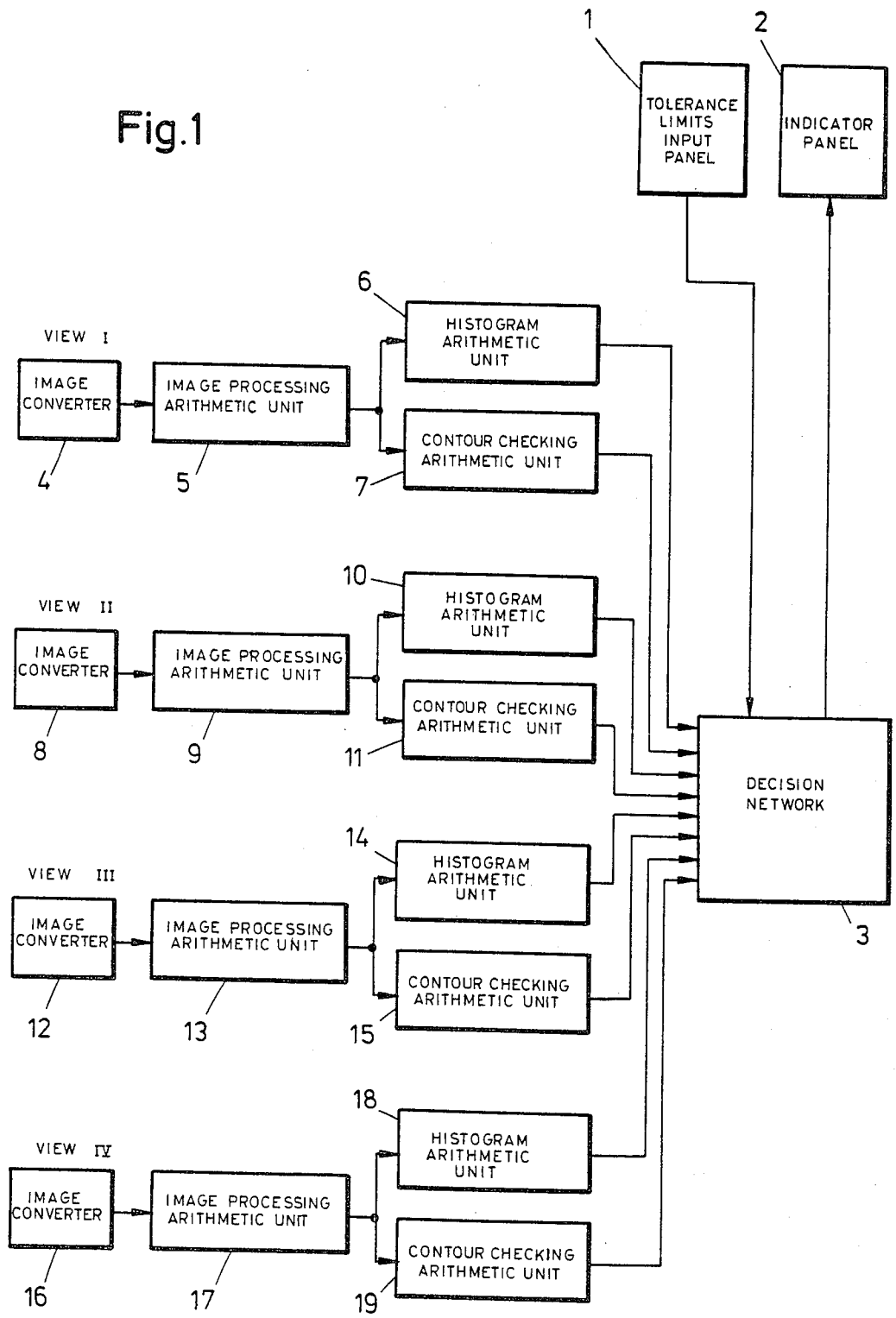
FIG. 1 is a block diagram of the inspection apparatus.

The inspection apparatus represented in the drawings serves for inspecting bottles and has four image-converters 4,8,12 and 16 for four different views of the bottle. Thus the image-converters 4 and 8 serve for the production of two side elevations offset by 90 degrees with respect to one another for the wall of the bottle, the image-converter 12 for inspecting the bottom of the bottle and the image-converter 16 for inspecting the mouth of the bottle. After each image-converter there is connected an image processing arithmetic unit 5,9,13 and 17, respectively which transmits its output signals respectively to histogram arithmetic units 6,10,14 and 18 respectively as well as to contour checking arithmetic units 7,11,15 and 19 respectively. These last-named arithmetic units transmit their output signals to a decision network 3, which is provided with an ejector unit for bottles which do not fulfill definite quality requirements. The quality requirements desired at any time are introduced into the decision network via a tolerance limits input panel 1. The decisions made by the decision network are indicated on an indicator panel 2 and picked up statistically on a fault adder which is, e.g., combined with the indicator.

Figure 2:
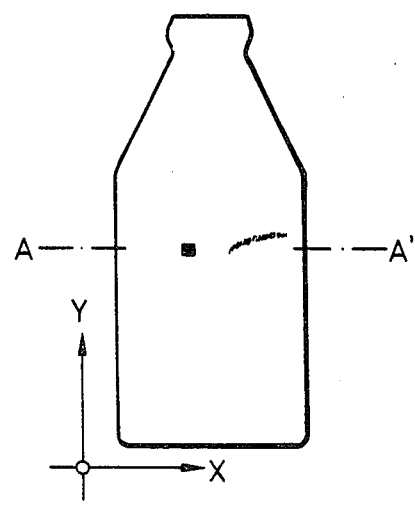
FIG. 2 shows diagrammatically the alignment of a bottle which is to be inspected, having two points of fault which are to be recognized.

As may be seen from FIG. 2, the bottles which are to be inspected are respectively aligned in such a way that a Y axis specifies the vertical direction of the bottle and also the alignment of the photoelectric elements in the image-converter in the form of a vertical line. An X axis specifies the direction of conveyance of the bottle. The bottom view of the bottle is produced by means of a rotating mirror, in which case a rectangular image of the circular area is effected on the image-convertor, and the Y axis specifies the radius and also the X axis specifies the rotary motion of the mirror. For the production of the view of the mouth of the bottle the Y axis lies transversely to the direction of conveyance of the bottle, whilst the X axis specifies the direction of conveyance of the bottle.

As is shown diagrammatically in FIG. 2, the bottle in the direction of the axis A—A' exhibits two points of fault which are to be detected, the one point of fault being a foreign body produced, e.g. by a paint spray and the other point of fault being one of frictional wear.

Figure 3:
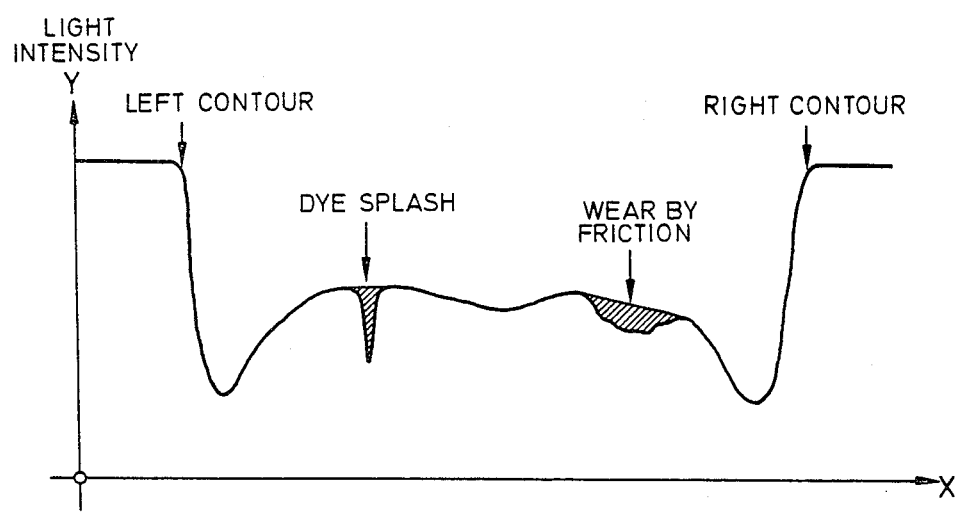
FIG. 3 shows a curve of intensity of the videosignal in the X direction.

In FIG. 3 a curve of intensity of the videosignal in the X direction along the axis A—A' is shown, in which the left hand and right hand contour of the bottle may be clearly recognized by a sharp drop in intensity or respectively a sharp rise in intensity from or respectively to the background brightness. Furthermore besides the usual fluctuations in intensity of the videosignal the alterations in intensity of the videosignal, caused by the two points of fault which are to be detected, can clearly be recognized.

As may be recognized from this diagrammatically illustrated videosignal, it is not sufficient to measure the absolute brightnesses since the basic colouring of the glass of the bottle influences negatively the certainty of the recognition of the fault. An evaluation of the gradients alone is unfavourable particularly in the vicinity of the contour. As an optimum solution the image spots picked up in the Y direction are stored temporarily and then for each Y value in the X direction neighbourhood operations are performed, which means the intensities between two image spots adjacent in the X direction are compared with one another. In that case an adaptive threshold determined by the basic brightness of the glass of the bottle is established in order to be able to emphasize, as compared with ordinary fluctuations in the intensity of the brightness, those fluctuations in intensity which correspond to points of fault. From these fluctuations in intensity specifying points of fault the following characteristic values are calculated: The width of the point of fault, the relative maximum amplitude, the integral of the intensity shown in FIG. 3 by the shaded area, as well as the mean relative blackening which is given by the integral of the intensity divided by the width. A correlation of the positions of the points of fault in the Y direction lets vertical irregularities such as moulding seams in the glass be recognized, which are not to be considered as points of fault.

Figure 4:
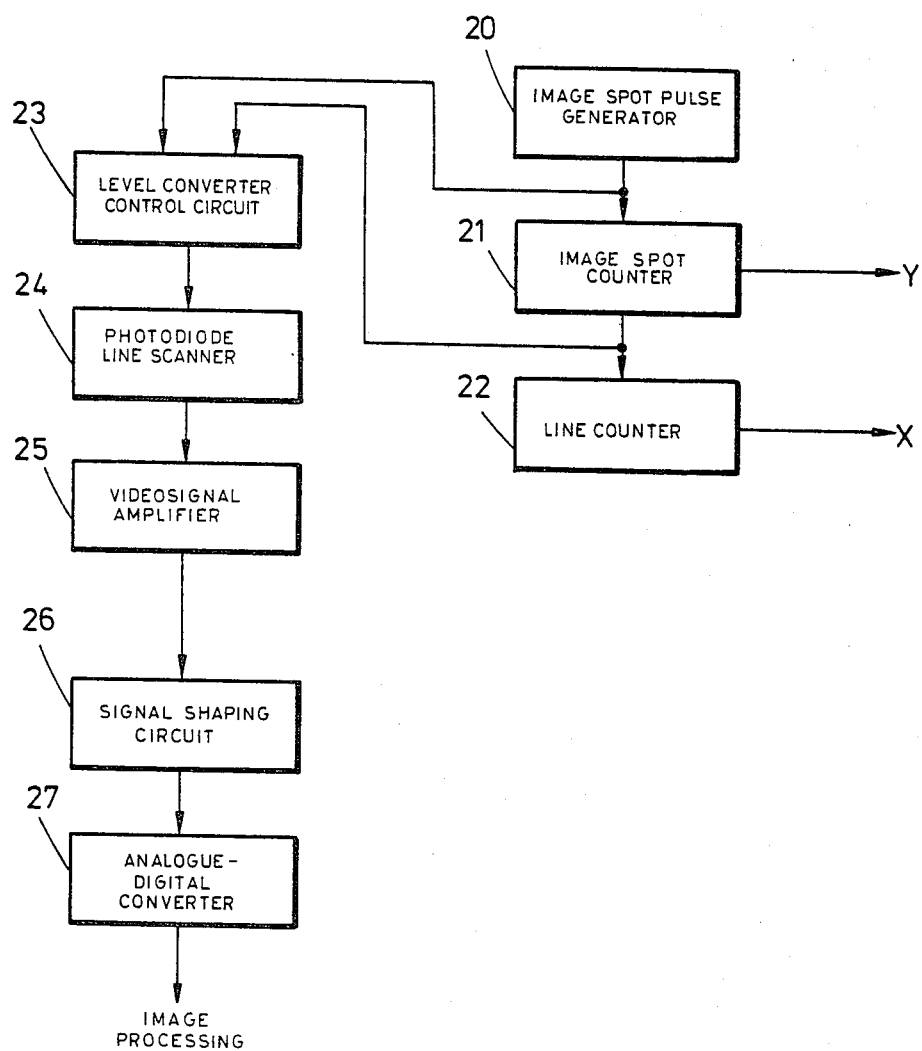
FIG. 4 is a block diagram of an image-converter.

The image-converter illustrated in greater detail in FIG. 4 exhibits as the principal item a photodiode line scanner 24, e.g., a so-called CCD-Line-Scan-Sensor having 256 photodiodes. Its output signal is fed via a videosignal amplifier 25 to a signal shaping circuit 26 in which by voltage-jamming a reference level is produced for the blackness of the videosignal. What is essential for the new method is the processing of all of the image spots in digital form, where it is not only a purely binary black-white distinction which is carried out, but on the contrary a real quantization in an analogue-digital converter 27, the digital signals being coded with 8 bits, which corresponds with 256 grey stages.

A level-converter-CCD control circuit 23 obtains timing signals from an image spot pulse generator 20 which also acts upon an image spot counter 21, the state of count of which at any time specifies the Y coordinate. A line counter 22 specifies by its state of count the respective X coordinate.

Figure 5:
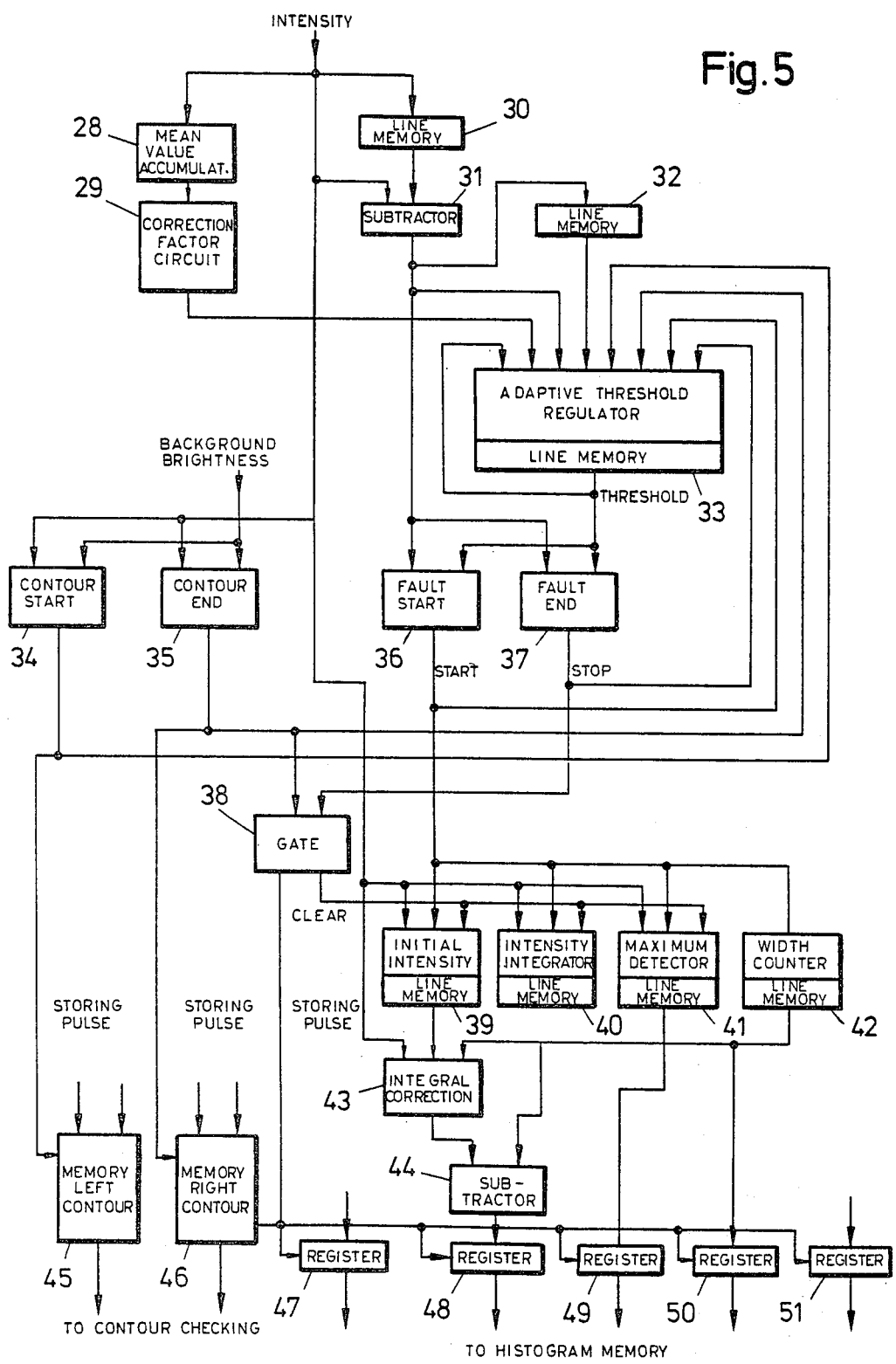
FIG. 5 is a block diagram of an image-processing arithmetic unit.

In the case of the image processing arithmetic unit shown in FIG. 5 the essential component is an adaptive threshold regulator 33 which ensures that inside the contour of the bottle only those alterations in intensity are evaluated, which also specify actual points of fault. The basic brightness of the glass of the bottle as well as shadings close to the contour through refraction are, on the contrary, eliminated. The threshold regulator 33 obtains its input information from a mean value accumulator 28 which integrates the brightness along a vertical scanning line and thereby acts as an illumination meter for the brightness of the bottle image, so that the threshold is correspondingly set in the threshold regulator 33. The output signal from the mean value accumulator 28 is modified in a circuit 29 by a correction factor corresponding with the characteristic of the image-converter.

Although the image spots are stated by the image-converter in columns, that is to say, in the Y direction, processing of the image spots in the X direction is more advantageous since the curve of intensity in the X direction is more homogeneous than in the Y direction, which is caused essentially by the alteration in contour of the bottle towards the mouth of the bottle. Furthermore the frictional wear which occurs in the case of most bottles also runs essentially in the X direction so that it is not recognized as a single point of fault as would be the case with evaluation in Y direction. For the establishment of alterations in intensity in the X direction a number of line stores are therefore necessary, which obtain as addresses all of the respective Y coordinates from the image spot counter 21. By means of these line stores 30, 32 neighbourhood operations in the X direction are possible, e.g., subtraction by means of a subtractor 31, adding or respectively integration or the finding of a maximum.

In the subtractor 31 the difference in intensity is determined between the image spot which has just been scanned and the image spot which has preceded it in each case at the same Y coordinate, whereby the so-called gradient results. The adaptive threshold regulator 33 obtains as further input quantities the instantaneous gradient, the old gradient, the old threshold, the states at the time of; contour start, contour end, start of the point of fault, end of the point of fault, as well as optionally the correction factor already mentioned previously for the image-converter characteristic. By means of circuits 34 and 35 for the contour start and the contour end these are determined by comparison of the intensity with the background brightness. By means of circuits 36,37 the start of a point of fault and the end of a point of fault are established by the gradient being compared with the adaptive threshold, a single large positive gradient or a repeated smaller positive gradient being evaluated as the start of the point of fault. For the end of a point of fault, the negative gradient obviously holds. Since the contour start is not to be evaluated as the start of a point of fault, the first end of a point of fault which occurs, that is, the end of the left hand edge shading is watched for. In the case of a start of a point of fault, by means of a start signal various arithmetical components are energized for the determination of definite characteristic quantities. These components are an initial-intensity store 39, an intensity integrator 40, a maximum-detector 41 and a width meter 42. The components 40, 41 and 42 work until the occurrence of the end of a point of fault, whilst the component 39 retains the intensity only at the start of the point of fault.

At the end of a point of fault a stop signal is generated. If at the same time the contour end is established by means of the circuit 35, the end of a point of fault which has been determined is recognized as the righthand edge shading, and, via a gate circuit 38, an erase pulse is transmitted to the arithmetical components 39,40,41 and 42. If on the contrary it is a question of a real end of a point of fault without any contour end, before the generation of the erase pulse the following values are, by means of a storage pulse, taken over into registers 47,48,49,50 and 51. The register 47 stores the Y coordinate, the register 51 stores the X coordinate, the register 50 stores the width of the point of fault, the register 49 stores the maximum value of the point of fault referred to the initial intensity, that is, the maximum relative blackening, and the register 48 stores the relative integral of the intensity, in which case a subtractor 44 subtracts from the integral of the intensity a trapezoidal area which is formed in an integral correction stage 43 out of the initial intensity, the final intensity and the width, as may be seen from FIG. 3 of the drawing. By means of this correction an error in measurement is eliminated, which would arise through fluctuations of the basic brightness over a large area because of different thickness of the glass.

The pulses emitted by the circuits 34 and 35 serve for the storage of the X and Y coordinates at the time in the stores 45 and 46 for the lefthand and righthand contours of the bottle.

Figure 6:
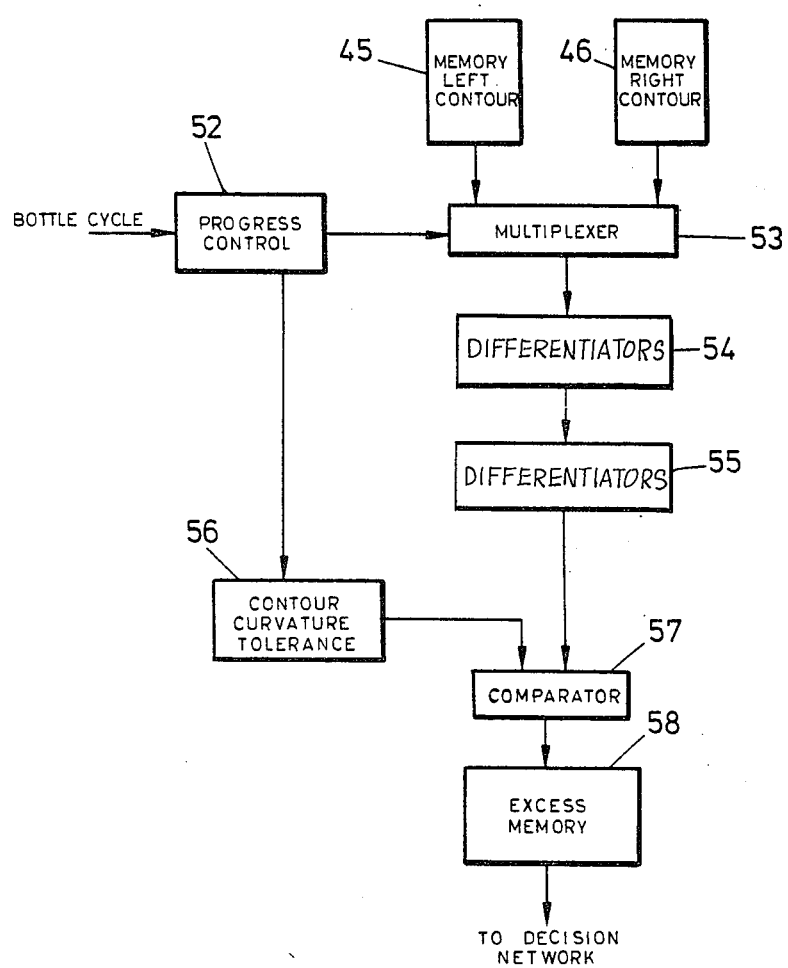
FIG. 6 is a block diagram of a contour-checking arithmatic unit.

In the case of the contour-checking arithmetic unit illustrated in FIG. 6 a progress control 52 is energized by means of a bottle cycle generated during the conveyance of the bottle, and for each Y coordinate reads out from the contour stores 45 and 46 the respective X coordinates via a multiplexer 53 and differentiates these twice by means of differentiators 54 and 55, after which in a comparator 57 it checks the curvature so obtained by comparison with the contour curvature tolerance stored in a store 56 according to Y coordinates, for whether the contour which has been determined lies within these tolerances or not, in which case each exceeding of the contour is stored in an excess store 58.

Figure 7:
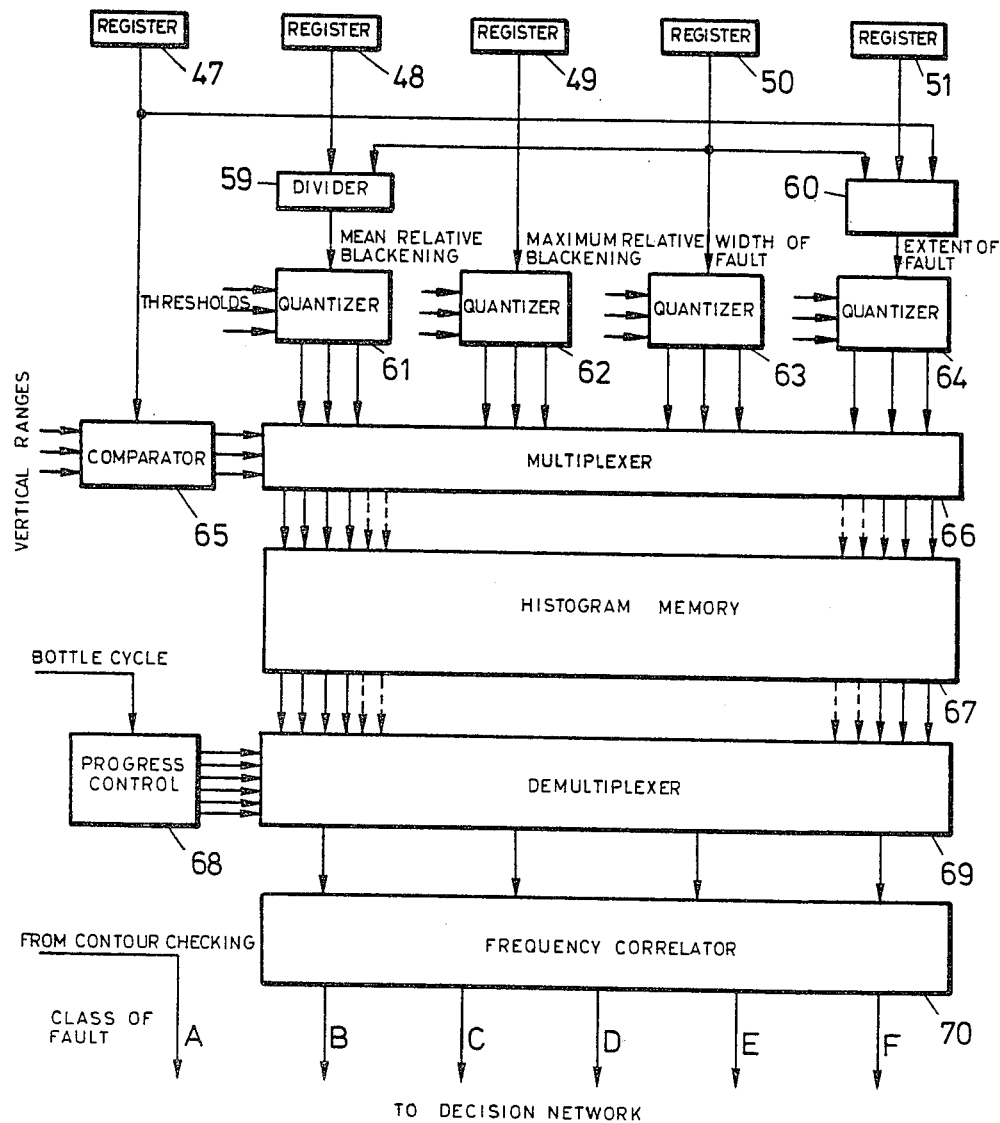
FIG. 7 is a block diagram of a histogram arithmatic unit.

Also in the case of the histogram arithmetic unit illustrated in FIG. 7 a progress control 68 is controlled by means of the bottle cycle. The progress control again controls any demultiplexer 69 which reads data out of a histogram store 67. The histogram store 67 stores frequencies of the characteristic quantities M1, M2, M3 and M4 established by means of the arithmetical component 39 to 42. These characteristic quantities are: M1 the mean relative blackening, M2 the maximum relative blackening, M3 the width of the point of fault and M4 the extent of the point of fault. The magnitudes of the individual characteristic quantities emitted by the image-processing arithmetic unit shown in FIG. 5 are in the case of the embodiment of the inspection apparatus being explained here, divided into three classes by means of thresholds, S1, S2 and S3 normalized specifically to faults. The fields $H_{11}$ to $H_{34}$ stated in the table below, state in each case the frequency at which the specified characteristic quantities have exceeded the previously mentioned thresholds.

|    | M1       | M2       | M3       | M4       |
|----|----------|----------|----------|----------|
| S1 | $H_{11}$ | $H_{12}$ | $H_{13}$ | $H_{14}$ |
| S2 | $H_{21}$ | $H_{22}$ | $H_{23}$ | $H_{24}$ |
| S3 | $H_{31}$ | $H_{32}$ | $H_{33}$ | $H_{34}$ |

A frequency correlator 70 checks the relationships of the frequencies $H_{11}$ to $H_{34}$ stored in the histogram store 67 and determines from these one or more fault classes B to F. These fault classes are: B at least one place worn by friction, C at least one scratch, D at least one severe vertical point of fault, E at least one splash or spots of paint, and F remains of labels or cement. A Class A fault means an incorrect contour, in which case this signal specifying the Class A fault is emitted from the excess store 58 out of the contour-checking arithmetic unit shown in FIG. 6.

The frequency table shown above may be laid out a number of times for different vertical regions in order, e.g. to evaluate differently the regions of a bottle affected especially by wear from friction. For doing this a comparator 65 and a multiplexer 66 are provided. The comparator is in this case energized by the register 47 which specifies the respective Y coordinate. By means of quantizers 61,62,63 and 64 the division into classes is performed by means of the thresholds S1, S2 and S3. A divider 59 divides the corrected relative integral of the intensity by the associated width of the point of fault and thereby determines the mean relative blackening of the point of fault. A vertical correlator 60 determines with the aid of its input quantities X, Y and the width, the respective overall extent of the point of fault.

Figure 8:
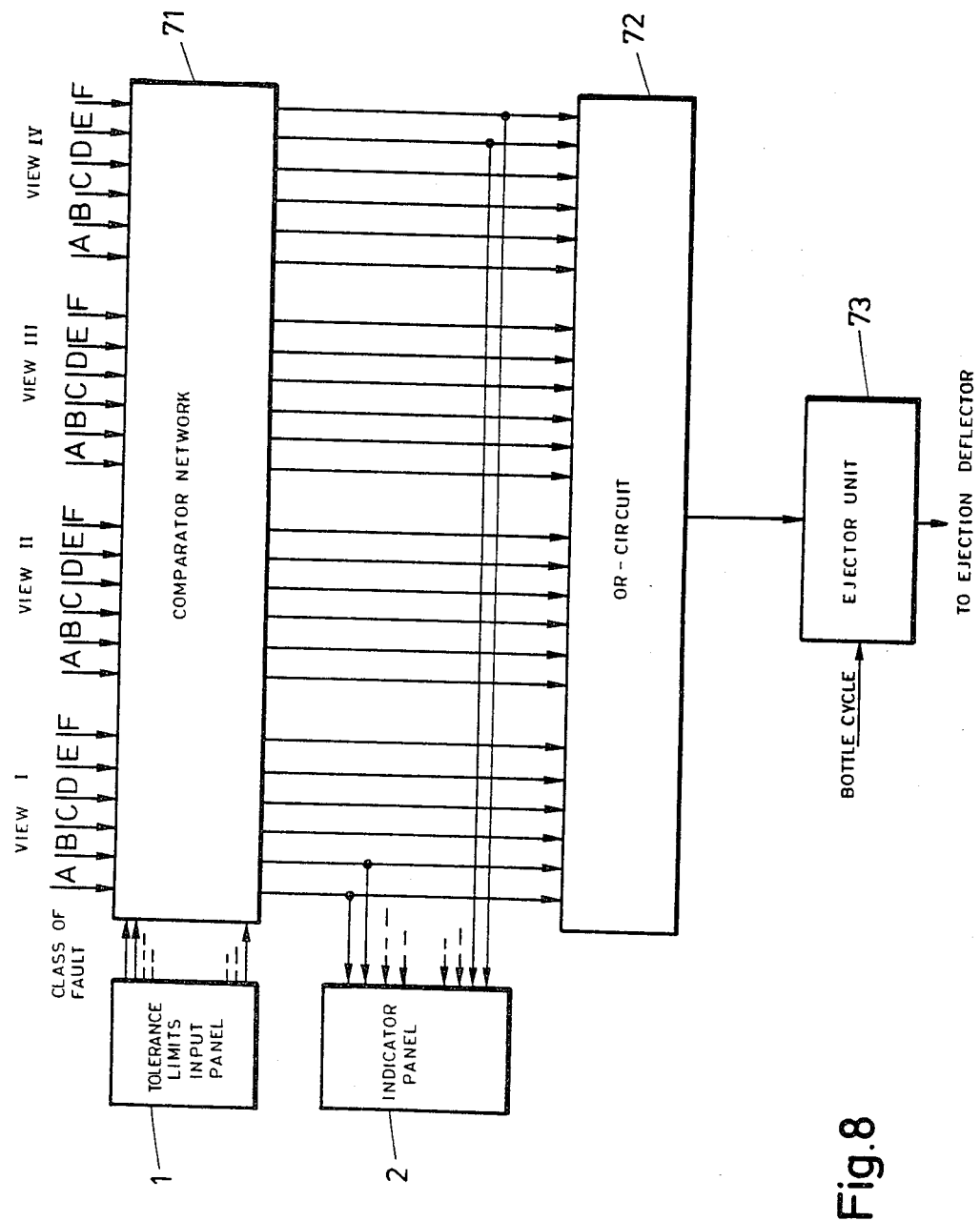
FIG. 8 is a block diagram of a decision network.

The decision network illustrated in FIG. 8 exhibits a comparator network 71 which obtains the results from the histogram arithmetic unit for all four views. By means of the tolerance limits input panel 1 a manual digital preset of the tolerance limits for each class of fault is effected for all of the views. In the comparator network 71 the exceeding of one or more tolerance limits is established and indicated on the indicator panel 2 by means, e.g. of indicator lamps.

The indicator panel 2 may contain fault adders which form over predetermined periods of time a fault statistic. By means of an OR-operation 72 a single ejector signal is issued to the ejector unit 73, whereupon in an associated delay stage an adaptation to the transit time is effected between the ejector signal and the path of conveyance of the bottle in question which is to be ejected, to an ejection deflector.

Obviously the arithmetic units and signal processing devices illustrated in the individual Figures in the form of block diagrams may be realized by a single computer, e.g., having digital microprocessors.

We claim:

1. In a method of inspecting an object, in particular a bottle, which is irradiated by a radiation that is received and converted into an electrical videosignal which is converted into a digital signal, points of fault in said object being recognised by alterations in intensity between said digital signals from two adjacent image spots the improvement wherein (1) only alterations in intensity which exceed a definite threshold level are recorded as the start of a point of fault and the end of a point of fault;

(2) for each of said points of fault one or more characteristic quantities are determined;

(3) said characteristic quantities are divided up into different classes corresponding with their magnitudes;

(4) the frequency distribution of the occurrence of said characteristic quantities in the different classes is established by adding; and (5) said frequency distribution established is correlated with predetermined frequency distributions in order to decide about the quality of said object.

2. A method as in claim 1, wherein said definite threshold level is set on the basis of that brightness of the image of said object and is determined by integration of the brightness along a vertical line of image spots.

3. A method as in claim 1, wherein said characteristic quantities are divided up into three different classes.

4. A method as in claim 1, wherein said frequency distribution for various vertical regions of said objects which are, e.g., particularly affected by frictional wear, is established by different ways of evaluation.

5. A method as in claim 1 for inspecting a bottle with a mouth, wherein said method is performed for four different views, namely, two side elevations offset by 90 degrees, a bottom view and a view of said mouth.

6. A method as in claim 1, wherein said videosignals in the vertical direction, are generated simultaneously and in the horizontal direction, are processed by comparison of the alteration in intensity between adjacent image spots.

7. A method as in claim 1, wherein from said videosignals, by establishing the alterations in intensity between the background and said object, the contour of said object is also determined and compared with definite contour values.

8. An inspection apparatus for carrying out said method as in one of the claims 1 to 7, having a photoelectric image-converter, an analogue-digital converter for an output signal from said image-converter, a register for temporary storage of said digital signal and a comparator for comparing an output signal from said analogue-digital converter with an output signal from said register, characterized by:

(a) an adaptive threshold regulator for step (1) of said method;

(b) an initial-intensity store, an intensity integrator a maximum-detector and a width-meter for step (2) of said method;

(c) quantizers connected after the foregoing respectively, for step (3) of said method;

(d) a histogram store for step (4) of said method; and (e) a frequency correlator for step (5) of said method.

9. An inspection apparatus as in claim 8, wherein between said quantizers and said histogram store a multiplexer is connected and is controlled by a comparator for the Y coordinates of said videosignals and predetermined vertical regions.

10. An inspection apparatus as in claim 8, wherein to said frequency correlator there is connected a comparator network which in turn is connected to a tolerance-limits input panel, and that to outputs from said comparator network there are connected an indicator panel and an ejector unit for ejecting objects not fulfilling a definite desired quality.

11. The method of claim 1 in which the recording step comprises integrating the electrical signal and varying the given threshold level in accordance with changes in the integrated signal.

12. In a method for inspecting an object such as a bottle by detecting radiation directed at the object, converting the detected radiation into an electrical signal representative of image spots from the object, and sensing alterations in the intensity of the signal from two adjacent image spots, the improvement comprising the steps of:

recording alterations in the intensity of the signal which exceed a predetermined threshold level to define the start of a point of fault and the end of a point of fault;

deriving from the alterations one or more characteristic quantities for each of the defined points of fault;

sorting each of the one or more characteristic quantities into a plurality of different classes depending upon their magnitudes;

counting the frequency of occurrence of each class of each of the one or more characteristic quantities; and correlating the counted frequencies of occurrence with established values to evaluate the quality of the object.

13. The method of claim 12, in which the converting step comprises converting the detected radiation into a multi-bit digital signal.

* * * * *